US008063265B2

(12) United States Patent
Beck et al.

(10) Patent No.: US 8,063,265 B2
(45) Date of Patent: Nov. 22, 2011

(54) HYDROGEL CAPABLE OF ABSORBING BLOOD AND/OR BODY FLUIDS

(75) Inventors: Martin Beck, Maxdorf (DE); Volker Frenz, Alteiningen (DE); Anna Kowalski, Frankenthal (DE); Elisabeth Selzer, Lumburgerhof (DE); Ernst Jürgen Bauer, Ludwigshafen (DE); Harald Keller, Ludwigshafen (DE); Bernhard Steinmetz, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 491 days.

(21) Appl. No.: 10/576,049

(22) PCT Filed: Oct. 28, 2004

(86) PCT No.: PCT/EP2004/012177
§ 371 (c)(1),
(2), (4) Date: Apr. 14, 2006

(87) PCT Pub. No.: WO2005/042039
PCT Pub. Date: May 12, 2005

(65) Prior Publication Data

US 2007/0066947 A1 Mar. 22, 2007

(30) Foreign Application Priority Data

Oct. 31, 2003 (DE) .................................. 103 51 267
Jun. 28, 2004 (DE) ......................... 10 2004 035 671

(51) Int. Cl.
*A61F 13/15* (2006.01)
*A61F 13/20* (2006.01)

(52) U.S. Cl. ........ 604/368; 604/367; 604/369; 604/403; 604/416; 422/27; 422/28; 422/40; 422/41; 422/180; 422/18; 516/135; 516/136; 516/137; 516/138; 516/9; 516/11; 516/13; 516/79; 516/80; 516/87; 516/905; 516/906; 521/86; 523/107; 523/111; 523/122; 523/200; 523/201; 523/204; 523/207; 523/209; 523/210; 523/212; 523/218; 523/310; 523/457; 523/513; 523/514; 523/521; 524/1; 524/441; 524/442; 524/444; 524/445; 524/492; 524/789; 524/859; 524/904; 524/917; 524/922; 588/9; 588/14; 588/249.5; 588/255; 525/195; 525/196; 525/934; 526/910; 526/932; 427/2.1; 427/446; 510/215; 510/223; 510/225; 510/473; 510/474; 510/476; 510/485; 510/486; 510/507; 428/570; 428/195.1; 428/40.9; 428/41.1; 428/41.5; 428/402; 428/403; 428/404; 428/405

(58) Field of Classification Search .................. 604/368, 604/367, 369, 416, 403; 422/27–28, 40–41, 422/18, 180; 516/135, 136, 137, 138, 9, 516/11, 13, 79–80, 87, 905, 906; 521/86; 523/107, 111, 122, 200–201, 204, 207, 209–210, 523/212, 218, 310, 457, 513, 514, 521; 524/1, 524/441–442, 444–445, 492, 789, 859, 904, 524/917, 922; 588/9, 249.5, 255, 7, 13–14, 588/18, 251; 525/195–196, 934; 526/910, 526/932; 427/2.1, 446; 510/215, 223, 225, 510/473, 474, 476, 485–486, 507; 428/570, 428/195.1, 40.9, 41.1, 41.4, 41.5, 402–405
See application file for complete search history.

(56) References Cited

U.S. PATENT DOCUMENTS

| | | | | | |
|---|---|---|---|---|---|
| 4,286,082 | A * | 8/1981 | Tsubakimoto et al. | ....... | 526/240 |
| 4,853,266 | A * | 8/1989 | Cullen | ......................... | 428/35.7 |
| 5,092,858 | A * | 3/1992 | Benson et al. | ................ | 604/319 |
| 5,306,487 | A * | 4/1994 | Karapasha et al. | .......... | 424/76.6 |
| 5,356,678 | A * | 10/1994 | Heitzhaus et al. | ........... | 428/35.6 |
| 5,595,731 | A * | 1/1997 | Vallieres | ...................... | 424/76.4 |
| 5,847,031 | A | 12/1998 | Klimmek et al. | | |
| 6,414,214 | B1 * | 7/2002 | Engelhardt et al. | ........... | 604/368 |
| 6,592,768 | B1 * | 7/2003 | Lepore et al. | ................. | 210/764 |
| 6,620,889 | B1 | 9/2003 | Mertens et al. | | |
| 6,623,848 | B2 * | 9/2003 | Brehm et al. | ................. | 428/327 |
| 6,916,864 | B2 * | 7/2005 | Gartner et al. | ................ | 523/337 |
| 2002/0128618 | A1 * | 9/2002 | Frenz et al. | ................... | 604/368 |
| 2003/0207997 | A1 | 11/2003 | Mertens et al. | | |

FOREIGN PATENT DOCUMENTS

| | | | |
|---|---|---|---|
| CA | 2179775 | C * | 6/1996 |
| CA | 2188838 | | 4/1998 |
| DE | 19909653 | | 9/2000 |
| EP | 0631768 | A1 * | 1/1995 |
| EP | 705643 | | 4/1996 |
| EP | 759460 | | 2/1997 |

(Continued)

OTHER PUBLICATIONS

Somasundaran et al; Encyclopedia of Surface and Colloidal Science, vol. 5, 2006, pp. 5324-5325. (five pages included), publication date Aug. 15, 2006.*
U.S. Appl. No. 09/674,263 entitled “Mechanically Stable Hydrogels”, filed Oct. 30, 2000.

*Primary Examiner* — Tatyana Zalukaeva
*Assistant Examiner* — Ginger T Chapman
(74) *Attorney, Agent, or Firm* — Marshall, Gerstein & Borun LLP

(57) ABSTRACT

A hydrogel having a floatability where from 40% to 90% of a solution and/or suspension to be thickened are thickened starting from the surface of the liquid and the rest of the solution and/or suspension to be thickened is thickened starting from the bottom of the container, a process for preparing the hydrogel and also its use for absorbing blood and/or body fluids, especially in hygiene articles, or for thickening aqueous solutions and/or suspensions, especially for thickening medical wastes.

13 Claims, No Drawings

FOREIGN PATENT DOCUMENTS

| | | | |
|---|---|---|---|
| EP | 1072630 | | 1/2001 |
| JP | 3-44367 | | 2/1991 |
| JP | 6-345980 | | 12/1994 |
| JP | 2001046423 | | 2/2001 |
| WO | WO-95/15771 | | 6/1995 |
| WO | WO-95/17455 | | 6/1995 |
| WO | WO9515771 | * | 6/1995 |
| WO | WO-95/19191 | | 7/1995 |
| WO | WO-98/42193 | | 10/1998 |
| WO | WO-99/55767 | | 11/1999 |
| WO | WO-00/10496 | | 3/2000 |

* cited by examiner

HYDROGEL CAPABLE OF ABSORBING BLOOD AND/OR BODY FLUIDS

CROSS-REFERENCE TO RELATED APPLICATIONS

This is the U.S. national phase application of International Application No. PCT/EP2004/012177, filed Oct. 28, 2004, which claims the benefit of German patent application No. 10 2004 035 671.8, filed Jun. 28, 2004, and German patent application No. 103 51 267.5, filed Oct. 31, 2003.

The present invention concerns hydrogels capable of absorbing blood and/or body fluids, a process for preparing hydrogels capable of absorbing blood and/or body fluids and also their use.

Further embodiments of the present invention are disclosed in the claims, the description and the examples. It will be appreciated that the aforementioned features of the present invention and the features of the present invention which will be described hereinbelow can be used not only in the particular combination stated, but also in other combinations without departing from the scope of the present invention.

Swellable hydrogel-forming polymers, known as superabsorbent polymers (SAPs) or superabsorbents for short, are known from the prior art.

Swellable hydrogel-forming polymers are in particular polymers of (co)polymerized hydrophilic monomers, graft (co)polymers of one or more hydrophilic monomers on a suitable grafting base, crosslinked cellulose ethers, crosslinked starch ethers, crosslinked carboxymethylcellulose, partially crosslinked polyalkylene oxide or natural products which are capable of swelling in aqueous fluids, such as guar derivatives for example. Such hydrogels are used as products capable of absorbing aqueous solutions to manufacture diapers, tampons, sanitary napkins and other hygiene articles, but also as water-retaining agents in market gardening or to thicken all kinds of wastes, especially medical wastes.

Swellable hydrogel-forming polymers are preferably capable of absorbing at least 10 times their own weight and preferably 20 times their own weight, based on the polymer used, of 0.9% by weight sodium chloride solution. This absorption is preferably achieved even under a pressure of 0.7 psi for example.

Swellable hydrogel-forming polymers are typically surface or gel postcrosslinked to improve their performance characteristics.

This postcrosslinking is known per se to one skilled in the art and preferably takes place in an aqueous gel phase or as surface postcrosslinking of the ground and classified polymeric particles.

Wastes, especially medical wastes and any kind of wastes contaminated with toxic, infectious, noxious or environmentally harmful materials have to be safely handled and transported. A superabsorbent is capable of immobilizing most harmful materials by taking up the liquid waste.

Medical wastes, especially hospital wastes from operating theaters, consist in particular of blood, body fluids and physiological saline (sodium chloride solution) which is used as an irrigation solution.

Conventional superabsorbents are optimized to absorb urine in hygiene articles, especially baby diapers. They always absorb substantially less blood compared with synthetic urine or physiological saline. When there is a substantial difference in the absorption of blood and physiological saline, different amounts of superabsorbent have to be added depending on the composition of the waste. This would mean in practice that either superabsorbent has to be substantially overdosed on principle or further superabsorbent has to be added as necessary. In the process, however, the actually sealed container would have to be repeatedly opened again as necessary, which takes additional time and represents a risk for people who have to handle the wastes.

It is therefore extremely advantageous to provide a superabsorbent which is capable of absorbing larger amounts of blood than commercially available superabsorbents. In the case of hospital wastes and medical wastes it is thus possible for solutions containing different amounts of blood to be solidified equally successfully.

A further aspect to the treatment of medical wastes with superabsorbents is the absorption rate. A very high absorption rate is not advantageous in the case of commercially available superabsorbents, particularly for baby diapers and incontinence products, since the fluid to be absorbed shall initially become distributed throughout the absorbent article. A superabsorbent having a very high rate of swell does not permit uniform distribution of the fluid in the hygiene article, but absorbs the entire fluid all at once. In contrast to conventional diapers, the rapid absorption of blood and/or body fluids is decisive in the case of medical wastes and feminine hygiene products, such as tampons, napkins and liners. The high absorption rate is important in order that the medical wastes may be very rapidly absorbed and hence immobilized.

Rapid solidification permits faster and safer handling of these wastes, for example in the course of transportation and storage.

A further advantageous behavior for the absorption of medical wastes is for a portion of the added superabsorbent to float on the surface of the fluid after it has been added to the solution and for a further portion to sink. This not only produces high-speed thickening, since the superabsorbent can swell from two interfaces, but also causes the surface of the fluid to be immediately blanketed with superabsorbent, making it difficult for materials such as viruses or bacteria for example to escape and especially avoiding splashing.

Rapid absorption is desirable for feminine hygiene products in order that the fluid be rapidly transported away from the body and stored in the hygiene article. A high retention is needed as well as rapid absorption and a high rate of swell.

Higher blood absorbence is a significant advantage for hygiene articles, since this permits the development of very effective and thin hygiene articles, which are preferred by the customer because of the wear comfort.

WO-A-99/55767 describes the use of aluminates for surface postcrosslinking of uncrosslinked or covalently crosslinked hydrogels. The reference teaches that the subsequent crosslinking improves gel strength and the absorption of fluids and blood, especially the absorbency under load value. But the swell rate and the floatability of the postcrosslinked hydrogel is unsatisfactory.

DE-A-199 09 653 teaches the application of an aqueous solution of a cation before or after a postcrosslinking reaction. Irrespectively of whether this treatment is carried out before or after the postcrosslinking reaction, the required properties cannot be achieved through this treatment.

WO-A-00/10496 describes an optimized material for absorbing blood by application of kaolinite to moistened superabsorbent and subsequent drying. The reference does not teach the combination of various coatings and on its own is insufficient for obtaining superabsorbent having the desired properties.

WO-A-95/17455 describes a porous superabsorbent which is capable of floating on water, even in the swollen state. This is due to dispersed nitrogen in the superabsorbent and cannot be brought about through an aftertreatment. Nor is it technically advantageous for the absorbent to fully float on the fluid.

EP-A-0 759 460 describes a material which was post-crosslinked again by addition of large amounts of a surface-postcrosslinking reagent. However, the higher degree of crosslinking does not lead to products having very high blood absorbence.

WO-A-95/19191 describes the production of superabsorbent materials having enhanced blood absorbence. Commercially available superabsorbents are additionally sprayed with polyols, such as polyethylene glycol or glycerol for example. The additional crosslinking of the polymer strands essentially takes the form of hydrogen bonds. The superabsorbents obtainable according to this reference are likewise not suitable for covering fluid surfaces because they lack any ability to float.

WO-A-98/42193, CA-A-2,188,838, WO-A-95/15771 and JP-A-03/044367 describe the use of superabsorbents with biocides, such as polyvinylpyrrolidone-iodine complexes and glutaraldehyde for example. The use takes the form of commercially available superabsorbents being mixed with a biocide. This leads neither to enhanced blood absorbence nor to an increased rate of absorption, but solely to disinfection of the thickened solution.

JP-A-06/345980 describes mixing superabsorbents with anionic surfactants. This does not enhance blood absorbence, nor does it increase the rate of absorption.

The present invention therefore had for its object to develop a specific superabsorbent which is optimally suitable for solidifying medical wastes. This superabsorbent shall provide safer handling of medical wastes through rapid absorption and also thickening or solidification.

The present invention further has for its object to provide a superabsorbent which combines a significantly enhanced blood absorbence with a rapid rate of swell. Such a superabsorbent would be suitable not only for thickening wastes of any kind, particularly medical wastes, but would also be very useful for absorbing fluids in the case of feminine hygiene products, such as tampons, napkins and panty liners.

The present invention further has for its object to provide a superabsorbent which, after addition to the solution, floats at least in part on the surface of the fluid while a further portion sinks. This not only produces high-speed thickening of liquid wastes, since the superabsorbent can swell from two interfaces, but also causes the surface of the fluid to be immediately covered with superabsorbent, making it difficult for entities such as viruses, bacilli or bacteria for example to escape.

We have found that this object is achieved, surprisingly, by the present invention's aftertreatment of known superabsorbent materials with hydrophobic and if appropriate hydrophilic compounds providing a higher rate of swell and enhanced blood absorbence. It is preferable to use hydrophobic and if appropriate hydrophilic compounds that are particulate. Useful hydrophobic compounds are in particular hydrophobicized pyrogenic silicas or hydrophobicized mixtures of pyrogenic silicas and pygrogenic aluminas. Useful hydrophilic compounds are in particular pyrogenic silicas or mixtures of pyrogenic silicas and pyrogenic aluminas.

Useful superabsorbent materials in the present invention's process are hydrogels or hydrogel mixtures. The water content of the hydrogels is preferably less than 20% by weight, more preferably less than 10% by weight and most preferably less than 1% by weight.

The terms "hydrophobic" and "hydrophilic" describe the wetting behavior of a surface with water. The contact angle of a water droplet is <90° on hydrophobic surfaces and >90° on hydrophilic surfaces. The contact angle is described for example in Colloid Polym. Sci., volume 259 (1981), pages 391 to 394.

For example, there are free hydroxyl groups on the particle surface of pyrogenic silicas. These hydroxyl groups are capable of forming hydrogen bonds. Pyrogenic silicas are hydrophilic as a result.

Reaction of pyrogenic silicas with trimethylchlorosilane for example can be used to convert the free hydroxyl groups into silyl ether groups. The silyl ether groups are no longer capable of forming hydrogen bonds. The pyrogenic silica has been rendered hydrophobic.

The amounts of hydrophilic and hydrophobic particles are advantageously chosen such that not only an increased rate of swell but also a partial floating of the superabsorbent particles on the fluid surface at the start of the swelling process is achieved. The additional coating with hydrophobic particles causes a portion of the superabsorbent to remain on the surface of the fluid to be thickened after all the superabsorbent needed has been added to the fluid to be thickened. A further portion of the superabsorbent thus treated slowly sinks into the solution to be thickened, since superabsorbents based on polyacrylates normally have a higher density than the solutions to be thickened. Without treatment, a commercially available superabsorbent would simply just sink into the solution immediately after addition.

The amount of hydrophobic particles used is to be individually adjusted in that the fraction of aftertreated superabsorbent floating on the liquid to be thickened increases as the level of hydrophobic particles increases. When, for example, the superabsorbent is aftertreated with hydrophilic materials as well, the amount of hydrophobic particles is to be increased if appropriate.

The amount of superabsorbent initially remaining partially on the surface means that the superabsorbent starts to swell not only upwardly from the bottom of the vessel but also downwardly from the surface into the solution to be thickened. This results at one and the same time in a plurality of technical advantages:

First, the solution to be thickened solidifies faster, since a superabsorbent which swells from both sides has to cover only half the swelling distance.

Secondly, the surface of the solution to be thickened is virtually immediately covered with superabsorbent. The superabsorbent then acts like a cork on the vessel and permits safe transportation and safe disposal of the wastes, since it is no longer possible for any liquid, contaminated constituents to escape during the transportation of the container.

The combination of hydrophilic and hydrophobic particles makes it possible to produce superabsorbents having a high rate of swell which at least partially float on water and aqueous surfaces at the start of the swelling process and are capable of rapidly solidifying the contents of a vessel holding medical wastes.

The present invention provides a process for aftertreating absorbent hydrogels, comprising the steps of:

aftertreating with at least one hydrophobic compound, preferably hydrophobic and/or hydrophobicized clay minerals, hydrophobicized aluminas and/or hydrophobicized silicas, more preferably hydrophobicized aluminas and/or hydrophobicized silicas, such as for example Aerosil® R 812, Aerosil® R 974 or Aerosil® R 8200 (Degussa Aktiengesellschaft, Germany).

if appropriate aftertreating with at least one hydrophilic compound, preferably hydrophilic clay minerals, aluminas and/or silicas, more preferably aluminas and/or silicas, such as for example Aerosil® 200 (Degussa Aktiengesellschaft, Germany).

The hydrophobic and hydrophilic compounds are preferably used in the form of particles. The average particle size is typically in the range from 0.001 to 10 μm, preferably in the range from 0.002 to 5 μm, more preferably in the range from 0.005 to 1 μm and most preferably in the range from 0.01 to 0.1 μm. The method of measurement for the particle size distribution is based on the analysis of diffraction spectra according to Fraunhofer. The analyses are standardly carried out using a Mastersizer S, a laser instrument from Malvern. Particular preference is given to pyrogenic aluminas, pyrogenic silicas or mixtures thereof. Very particular preference is given to mixtures of pyrogenic silicas with greater than 0% to 20% by weight of pyrogenic alumina and also to pyrogenic silicas. The average primary particle size is preferably in the range from 5 to 50 nm and more preferably in the range from 10 to 20 nm, and the specific surface area is preferably in the range from 10 to 1000 $m^2/g$ and more preferably in the range from 80 to 380 $m^2/g$. The amounts used are typically in the range from 0.005% to 20% by weight, preferably in the range from 0.05% to 10% by weight, more preferably in the range from 0.1% to 5% by weight and most preferably less than 1% by weight of hydrophobic, hydrophobicized or hydrophilic compound based on the absorbent hydrogel.

Hydrophobicized aluminas and/or silicas are obtainable for example by reaction of hydrophilic aluminas and/or silicas with hexamethyldisilazane or dimethyldichlorosilane.

The hydrophobic and hydrophilic compounds are preferably mixed with the dried water-absorbing hydrogel. Dry means preferably a water content of less than 20% by weight and more preferably of less than 10% by weight. The type of mixing is not subject to any restrictions, but preference is given to using reaction mixers or mixing and drying ranges, such as for example Lödige® mixers, BEPEX® mixers, NAUTA® mixers, SCHUGGI® mixers, NARA® dryers and PROCESSALL®. Fluidized bed dryers can also be used moreover. The mixing is advantageously carried out using a residence time from 1 to 180 minutes, preferably from 2 to 20 minutes and more preferably from 5 to 20 minutes and a speed from 10 to 1000 rpm, preferably from 50 to 300 rpm and more preferably from 50 to 250 rpm.

The invention further provides a process for aftertreating absorbent hydrogels, comprising the steps of:

- aftertreating with at least one multivalent metal ions, solutions of multivalent metal ions, water-soluble cationic polymers and/or solutions of water-soluble polymers, preferably multivalent metal ions, such as for example $Al^{3+}$, $Fe^{2+}$, $Fe^{3+}$, $Ti^{3+}$, $Ti^{4+}$, $Co^{2+}$, $Ni^{2+}$, $Cr^{3+}$, $Mn^{2+}$, $Zn^{2+}$, $Mg^{2+}$, $Ca^{2+}$, $Zr^{3+}$, $Zr^{4+}$, more preferably $Al^{3+}$.
- aftertreating with at least one hydrophobic compound, preferably hydrophobic and/or hydrophobicized clay minerals, hydrophobicized aluminas and/or hydrophobicized silicas, more preferably hydrophobicized aluminas and/or hydrophobicized silicas, such as for example Aerosil® R 812, Aerosil® R 974 or Aerosil® R 8200 (Degussa Aktiengesellschaft, Germany).
- if appropriate aftertreating with at least one hydrophilic compound, preferably hydrophilic clay minerals, aluminas and/or silicas, more preferably aluminas and/or silicas, such as for example Aerosil® 200 (Degussa Aktiengesellschaft, Germany).
- if appropriate aftertreating with at least one anionic, cationic and/or nonionic surfactant, preferably a nonionic surfactant, such as for example sorbitan esters having an HLB value from 2 to 18, particular preference being given to Span® 80 (Uniqema, Netherlands).

The counterions to the multivalent metal ions are not subject to any restriction, but when a solvent is used there is a preference for counterions which ensure adequate solubility, preference being given to sulfate. The metal ions are preferably metered as a solution. Water is a particularly preferred solvent. The concentration of the multivalent metal ion in the aqueous solution is typically from 1% to 20% by weight and preferably from 2% to 10% by weight.

The amount of the multivalent metal ion used is typically in the range from 0.05% to 4% by weight, preferably in the range from 0.1% to 2% by weight and more preferably in the range from 0.2% to 1% by weight based on the absorbing hydrogel.

The surfactants are preferably metered as a solution. Diethylene glycol monobutyl ether is a particularly preferred solvent. The concentration of the surfactant in the solution is typically in the range from 5% to 70% by weight, preferably in the range from 10% to 50% by weight and more preferably in the range from 20% to 30% by weight.

The amount of surfactant used is typically in the range from 0.01% to 4% by weight, preferably in the range from 0.05% to 2% by weight and more preferably in the range from 0.1% to 1% by weight based on the absorbing hydrogel.

The order in which the aftertreating agents are metered is not subject to any restriction, but preference is given to the order

- multivalent metal ions, solutions of multivalent metal ions, water-soluble cationic polymers and/or solutions of water-soluble polymers,
- hydrophilic and hydrophobic compounds together or separately in any order,
- surface-active compounds, such as surfactants for example, and also solutions thereof, preferably only multivalent metal ions and hydrophobic compounds being used for the aftertreatment.

The dissolved aftertreating agents are preferably sprayed onto the dried water-absorbing hydrogel and mixed. The type of mixing is not subject to any restrictions, but preference is given to using reaction mixers or mixing and drying ranges, such as for example Lödige® mixers, BEPEX® mixers, NAUTA® mixers, SCHUGGI® mixers, NARA® dryers and PROCESSALL®. Fluidized bed dryers can also be used moreover. The mixing is advantageously carried out using a residence time from 1 to 180 minutes and preferably from 2 to 15 minutes and a speed from 10 to 1000 rpm, preferably from 50 to 300 rpm and more preferably from 50 to 250 rpm.

The last step may be followed by drying. Drying may take place in the mixer itself, by heating the jacket or introducing a stream of warm air. It is similarly possible to use a downstream dryer, such as for example a tray dryer, a rotary tube oven or a heatable screw. But it is also possible for example to utilize an azeotropic distillation as a drying process.

Preferred drying temperatures in the process of the present invention are in the range from 50 to 250° C., preferably in the range from 50 to 200° C. and more preferably in the range from 50 to 150° C. The residence time at this temperature in the reaction mixer or dryer is advantageously below 30 minutes and preferably below 10 minutes.

The drying is preferably carried out at reduced pressure, preferably at less than 500 mbar and more preferably at less than 200 mbar and, if appropriate, supported by a dry gas stream, preferably nitrogen, in an amount from 20 to 1000 l/kgh and preferably from 100 to 250 l/kgh.

Preferably, the absorbent hydrogels are additionally aftertreated with a hydrophilic organic compound in the process of the present invention. Hydrophilic organic compounds improve the fixing of the particulate aftertreating agents on the superabsorbent. Useful hydrophilic organic compounds include for example lower water-soluble polyols having an average molecular weight in the range from 100 to 6000 g/mol, preferably in the range from 200 to 3000 g/mol and more preferably in the range from 250 to 1000 g/mol.

Preferred hydrophilic organic compounds are dendritic polymers, highly branched polymers such as for example polyglycerols, polyethylene glycols, polypropylene glycols, random or block copolymers of ethylene oxide and propylene oxide. Useful compounds for this purpose further include polyethoxylates or polypropoxylates of polyhydroxy compounds, such as glycerol, sorbitol, trimethylolpropane, trimethylolethane, pentaerythritol. Examples thereof are n-tuply ethoxylated trimethylolpropane or glycerol, n being an integer between 1 and 100. Further examples are block copolymers of fully n-tuply ethoxylated and then m-tuply propoxylated trimethylolpropane or glycerol, n being an integer between 1 and 40 and m being an integer between 1 and 40. The order of the blocks can also be the other way around.

The hydrophilic organic compound can be added before, during or after each of the aftertreating steps, preferably before the aftertreatment with the hydrophobic organic compound and more preferably together with the multivalent metal ion.

The hydrophilic organic compound is liquid at 23° C. and has a 23° C. viscosity of less than 3000 mPas, preferably less than 1500 mPas, more preferably less than 1000 mPas, even more preferably less than 500 mPas and most preferably less than 300 mPas.

The hydrophilic organic compound is used in an amount based on the dried hydrogel that is in the range from 0.01% to 2% by weight, preferably in the range from 0.1% to 1% by weight and more preferably in the range from 0.35% to 0.75% by weight.

The invention further provides crosslinked water-absorbing polymers which, for example, are obtainable by the process of the present invention, especially absorbing hydrogels having a blood absorbence of at least 10 g/g, preferably of at least 15 g/g, more preferably of at least 19 g/g, even more preferably of at least 22 g/g and particularly preferably of at least 25 g/g, a solidification time of less than 120 seconds, preferably less than 100 seconds, more preferably of less than 90 seconds, even more preferably of less than 80 seconds and particularly preferably of less than 70 seconds, and/or a floatability where from 10% to 95%, preferably from 40% to 90% and more preferably from 65% to 80% of the solution containing the blood and/or body fluids to be thickened are thickened starting from the surface of the fluid, and also their use for absorbing blood and/or body fluids, especially in hygiene articles, or for thickening aqueous solutions and/or suspensions, especially for thickening medical wastes.

The present invention further provides hygiene articles comprising the superabsorbent of the present invention.

The swellable hydrogel-forming polymers which can be used in the process of the present invention are in particular polymers of crosslinked (co)polymerized hydrophilic monomers, polyaspartic acid, graft (co)polymers of one or more hydrophilic monomers on a suitable grafting base, crosslinked cellulose ethers, crosslinked starch ethers or natural products which are swellable in aqueous fluids, such as guar derivatives for example. Preferably, the polymer to be crosslinked is a polymer which comprises structure units which derive from acrylic acid or esters thereof or which were obtained by graft copolymerization of acrylic acid or acrylic esters on a water-soluble polymeric matrix. These hydrogels will be known to one skilled in the art and are described for example in U.S. Pat. No. 4,286,082, DE-C-27 06 135, U.S. Pat. No. 4,340,706, DE-C-37 13 601, DE-C-28 40 010, DE-A-43 44 548, DE-A-40 20 780, DE-A-40 15 085, DE-A-39 17 846, DE-A-38 07 289, DE-A-35 33 337, DE-A-35 03 458, DE-A-42 44 548, DE-A-42 19 607, DE-A-40 21 847, DE-A-38 31 261, DE-A-35 11 086, DE-A-31 18 172, DE-A-30 28 043, DE-A-44 18 881, EP-A-0 801 483, EP-A-0 455 985, EP-A-0 467 073, EP-A-0 312 952, EP-A-0 205 874, EP-A-0 499 774, DE-A 26 12 846, DE-A-40 20 780, EP-A-0 205 674, U.S. Pat. No. 5,145,906, EP-A-0 530 438, EP-A-0 670 073, U.S. Pat. No. 4,057,521, U.S. Pat. No. 4,062,817, U.S. Pat. No. 4,525,527, U.S. Pat. No. 4,295,987, U.S. Pat. No. 5,011,892, U.S. Pat. No. 4,076,663 or U.S. Pat. No. 4,931,497.

Examples of hydrophilic monomers suitable for preparing these swellable hydrogel-forming polymers are acids which are capable of addition polymerization, such as acrylic acid, methacrylic acid, vinylsulfonic acid, vinylphosphonic acid, maleic acid, maleic anhydride, fumaric acid, itaconic acid, 2-acrylamido-2-methylpropanesulfonic acid, 2-acrylamido-2-methylpropanephosphonic acid and also their amides, hydroxyalkyl esters and amino- or ammonio-containing esters and amides and also the alkali metal and/or ammonium salts of the acid-functional monomers. It is further possible to use water-soluble N-vinylamides such as N-vinylformamide or else diallyldimethylammonium chloride. Preferred hydrophilic monomers are compounds of the general formula I

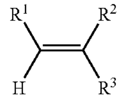

(I)

where $R^1$ is hydrogen, methyl, ethyl or carboxyl, $R^2$ is —$COOR^4$, hydroxysulfonyl or phosphonyl, a phosphonyl group esterified with a $C_1$-$C_4$-alkanol, or a group of the formula II

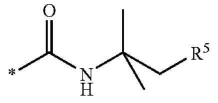

(II)

$R^3$ is hydrogen, methyl or ethyl, $R^4$ is hydrogen, $C_1$-$C_4$-aminoalkyl, $C_1$-$C_4$-hydroxyalkyl, alkali metal ion or ammonium ion, and $R^5$ is a sulfonyl group, a phosphonyl group or a carboxyl group or a respective alkali metal or ammonium salt.

Examples of $C_1$-$C_4$-alkanols are methanol, ethanol, n-propanol, isopropanol or n-butanol.

Particularly preferred hydrophilic monomers are acrylic acid and methacrylic acid and also their alkali metal or ammonium salts, for example sodium acrylate, potassium acrylate or ammonium acrylate.

Suitable grafting bases for hydrophilic hydrogels which are obtainable by graft copolymerization of olefinically unsaturated acids or their alkali metal or ammonium salts can be of natural or synthetic origin. Examples are starch, cellulose or cellulose derivatives and also other polysaccharides and oligosaccharides, polyalkylene oxides, especially polyethylene oxides and polypropylene oxides, and also hydrophilic polyesters.

Suitable polyalkylene oxides have for example the formula III

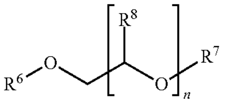

(III)

where $R^6$, $R^7$ are independently hydrogen, alkyl, alkenyl or aryl, $R^8$ is hydrogen or methyl, and n is an integer from 1 to 10 000.

$R^6$ and $R^7$ are each preferably hydrogen, $C_1$-$C_4$-alkyl, $C_2$-$C_6$-alkenyl or phenyl.

Preferred hydrogels are in particular polyacrylates, polymethacrylates and also the U.S. Pat. No. 4,931,497, U.S. Pat. No. 5,011,892 and U.S. Pat. No. 5,041,496 graft polymers.

The swellable hydrogel-forming polymers have preferably been crosslinked, i.e., they comprise compounds having at least two double bonds which have been polymerized into the polymeric network. Suitable crosslinkers are in particular N,N'-methylenebisacrylamide and N,N'-methylenebismethacrylamide, esters of unsaturated mono- or polycarboxylic acids of polyols, such as diacrylate or triacrylate, for example butanediol or ethylene glycol diacrylate or methacrylate and also trimethylolpropane triacrylate and allyl compounds such as allyl(meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. The process of the present invention can further utilize hydrogels which are prepared using polyallyl ethers as a crosslinker and by acidic homopolymerization of acrylic acid. Suitable crosslinkers are pentaerythritol triallyl and tetraallyl ethers, polyethylene glycol diallyl ether, ethylene glycol diallyl ether, glycerol dially ether, glycerol triallyl ether, polyallyl ethers based on sorbitol, and also ethoxylated variants thereof.

The preferred methods of making the base polymer which can be used in the process of the present invention are described in "Modern Superabsorbent Polymer Technology", F. L. Buchholz and A. T. Graham, Wiley-VCH, 1998, pages 77 to 84. Particular preference is given to base polymers which are prepared in a kneader, as described for example in WO-A-01/38402, or on a belt reactor, as described for example in EP-A-0 955 086.

The water-absorbing polymer is preferably a polymeric acrylic acid or a polyacrylate. This water-absorbing polymer can be prepared by a process known from the literature. Preference is given to polymers which comprise crosslinking comonomers in amounts from 0.001 to 10 mol % and preferably 0.01 to 1 mol %, but very particular preference is given to polymers which were obtained by free-radical polymerization and where a polyfunctional ethylenically unsaturated free-radical crosslinker was used which additionally bears at least one free hydroxyl group (such as for example pentaerythritol triallyl ether or trimethylolpropane diallyl ether).

The swellable hydrogel-forming polymers are preparable by addition polymerization processes known per se. Preference is given to addition polymerization in aqueous solution conducted as a gel polymerization. It involves for example 15% to 50% by weight aqueous solutions of one or more hydrophilic monomers and if appropriate of a suitable grafting base being addition polymerized in the presence of a free-radical initiator by utilizing the Trommsdorff-Norrish effect (Makromol. Chem. 1, 169 (1947)), preferably without mechanical mixing. The addition polymerization reaction may be carried out in the temperature range between 0 and 150° C. and preferably between 10 and 100° C., not only at atmospheric pressure but also at superatmospheric or reduced pressure. As usual, the polymerization can also be carried out in a protective gas atmosphere, preferably under nitrogen. The addition polymerization may be induced using high-energy electromagnetic rays or the customary chemical addition polymerization initiators, for example organic peroxides, such as benzoyl peroxide, tert-butyl hydroperoxide, methyl ethyl ketone peroxide, cumene hydroperoxide, azo compounds such as azodiisobutyronitrile and also inorganic peroxo compounds such as $(NH_4)_2S_2O_8$ or $K_2S_2O_8$ or $H_2O_2$. They may be used if appropriate in combination with reducing agents such as sodium hydrogensulfite and iron(II) sulfate or redox systems, where the reducing component included is an aliphatic or aromatic sulfinic acid, such as benzenesulfinic acid and toluenesulfinic acid or derivatives of these acids, such as Mannich adducts of sulfinic acids, aldehydes and amino compounds, as described in DE-A-13 01 566. The performance characteristics of the polymers can be further improved by postheating the polymer gels in the temperature range from 50 to 130° C. and preferably from 70 to 100° C. for several hours.

The gels obtained are neutralized for example to 0 to 100 mol % preferably 25 to 100 mol % and more preferably to 50 to 85 mol %, based on monomer used, for which the customary neutralizing agents can be used, preferably alkali metal hydroxides, alkali metal oxides, but more preferably sodium hydroxide, sodium carbonate and sodium bicarbonate.

Neutralization is typically achieved by mixing the neutralizing agent as an aqueous solution or else preferably as a solid into the gel. For this, the gel is mechanically comminuted, for example by means of a meat grinder, and the neutralizing agent is sprayed on, scattered on or poured on and then carefully mixed in. The gel mass obtained can then be repeatedly passed through the meat grinder for homogenization. The neutralized gel mass is then dried with a belt or can dryer until the residual moisture content is preferably below 10% by weight and especially below 5% by weight. The dried hydrogel is subsequently ground and sieved, and the grinding can typically be carried out using roll mills, pin mills or swing mills. The particle size of the sieved hydrogel is preferably in the range from 45 to 1000 μm, more preferably in the range from 45 to 850 μm, even more preferably in the range from 100 to 800 μm and yet more preferably in the range from 100 to 700 μm.

The postcrosslinking of hydrogels and superabsorbents is typically carried out by spraying a solution of the surface postcrosslinker onto the dry base polymer powder. After spraying, the polymeric powder is thermally dried, and the crosslinking reaction can take place not only before but also during the drying.

The spraying with a solution of the crosslinker is preferably carried out in reaction mixers or mixing and drying ranges, such as for example Lödige® mixers, BEPEX® mixers, NAUTA® mixers, SCHUGGI® mixers, NARA® dryers and PROCESSALL®. Fluidized bed dryers can be used as well in addition.

Drying may take place in the mixer itself, by heating the jacket or introducing a stream of warm air. It is similarly possible to use a downstream dryer, such as for example a tray dryer, a rotary tube oven or a heatable screw. But it is also possible for example to utilize an azeotropic distillation as a drying process.

Preferred drying temperatures are in the range from 50 to 250° C., preferably in the range from 50 to 200° C. and more preferably in the range from 50 to 150° C. The preferred residence time at this temperature in the reaction mixer or dryer is below 30 minutes and more preferably below 10 minutes.

The crosslinker is preferably dissolved in solvents which are not self-reactive, preferably in lower alcohols, such as for example methanol, ethanol, propanediol, ethylene glycol, most preferably in aqueous solutions of such suitable alcohols, in which case the alcohol content of the solution is in the range from 10% to 90% by weight and more preferably in the range from 40% to 60% by weight.

The crosslinker is used in an amount from 0.01% to 1% by weight, based on the polymer used, and the crosslinker solution itself is used in an amount from 1% to 20% by weight and preferably from 5% to 15% by weight, based on the polymer used.

The AUL 0.7 psi value [g/g] of the postcrosslinked water-absorbing polymers of the present invention can be measured by the method reported in DE-A-199 09 653 and is preferably greater than 10, especially greater than 15, more preferably greater than 20, especially greater than 25 and especially preferably greater than 30.

The present invention's aftertreated hydrogels capable of absorbing aqueous fluids are particularly useful for thickening aqueous solutions and/or suspensions, preferably for thickening aqueous waste solutions and/or waste suspensions, such as for example medical and/or radioactive wastes, most preferably for thickening medical waste solutions and/or waste suspensions.

The present invention's aftertreated hydrogels capable of absorbing aqueous fluids are also useful for absorbing blood and/or body fluids in hygiene articles, such as for example incontinence articles, napkins, tampons, liners. To this end, the present invention's aftertreated hydrogels capable of absorbing aqueous fluids can be processed with fibers, such as cellulose for example, and also fibrous web to form absorbing composites.

An aftertreatment with hydrophobic and hydrophilic materials ensures a uniform distribution of the superabsorbent in the container when treating at least partially liquid wastes, especially at least partially liquid medical wastes, in that at least a portion of the superabsorbent will initially float on the surface of the solution.

The present invention further provides mixtures of products prepared by the present invention's process with biocidal, antimicrobial and/or antibacterial materials and/or perfume or scent materials, stabilizers, dyes, pH indicators and/or other auxiliaries.

To determine the quality of the present invention's aftertreatment, the dried hydrogel is tested by test methods described hereinbelow:

Methods:

Blood Absorbence (BA):

This method is used to determine the blood absorbence of superabsorbents within 30 minutes.

Experimental Setup:

- plastics container, round, internal diameter 50±0.2 mm, internal height 20±0.2 mm (container I)
- plastics cylinder with net (400 mesh=36 μm size holes), internal diameter 25±0.2 mm, height 40±0.2 mm (container II)
- petri dish with lid, diameter 140 mm, height 75 mm
- stopwatch
- analytical balance accurate to ±0.0001 g
- defibrinated sheep blood from Oxoid GmbH, D-46467 Wesel Procedure:

0.2 g of superabsorbent is weighed into container II, the empty weight of which was determined beforehand. Container I is charged with 15 g of defibrinated sheep blood. Container II is then placed in container I, and this setup is placed in the petri dish, the petri dish is sealed with the lid and the stopwatch is started. After 30 minutes, container II is removed from container I, the outside of container II is cleaned with a cloth and the weight of container II is subsequently determined. The difference between this weight and the empty weight of container II and also the mass of superabsorbent used (0.2 g) is used to compute the amount of blood absorbed and hence the blood absorbence.

Calculation:

$$\frac{\text{blood absorbed [g]}}{\text{weight of superabsorbent [g]}} = \text{blood absorbence [g/g]}$$

Solidification Time (ST):

This method is used as a laboratory method to determine the time which a superabsorbent needs to solidify 2 liters of a 0.9% by weight NaCl solution and thus constitutes the on-spec laboratory test for thickening hospital or medical wastes.

Experimental Setup:

- cylindrical glass vessel having an internal diameter of 12 cm, a height of 28 cm and an internal volume of 3 liters
- 2 liters of 0.9% by weight NaCl solution, prepared by dissolving 90 g of NaCl in 9910 ml of completely ion-free water
- stopwatch Procedure:

The glass container is charged with 2 liters of the 0.9% by weight NaCl solution. Then 67 g of superabsorbent are added to the solution all at once and the time to complete solidification of the solution is measured.

Floatability (SV):

The floatability of the superabsorbent to be investigated is determined together with the solidification time. A visual determination is performed during the measurement.

Superabsorbent particles which float on the surface of the liquid swell from the surface of the liquid in the direction of the container bottom. Superabsorbent particles which sink to the bottom swell starting from the container bottom in the direction of the surface of the liquid.

A floatability of 0% is assigned when all superabsorbent particles immediately sink to the bottom and the liquid to be thickened is exclusively thickened starting from the container bottom. The swell front migrates from the container bottom to the surface of the liquid.

A floatability of 100% is assigned when all superabsorbent particles float on the surface of the liquid and the liquid to be thickened is exclusively thickened starting from the surface of the liquid. The swell front migrates from the surface, of the liquid to the container bottom.

A floatability of 50% is assigned when some superabsorbent particles immediately sink to the bottom and some float on the surface of the liquid, so that the two swell fronts meet in the middle between the container bottom and the surface of the liquid.

EXAMPLES

Examples 1 to 31

A Lödige® plowshare M5/20 laboratory batch mixer was charged with 1 kg of commercially available hydrogel capable of absorbing aqueous fluids (Hysorb F) and if appropriate the stated amount of aluminum sulfate was sprayed on as a 26.8% by weight aqueous solution and mixed in for 10 minutes and if appropriate the stated amount of Aerosil® R 812, Aerosil® R 974, Aerosil® R 8200 and/or Aerosil® 200 was added and mixed in for 15 minutes and if appropriate the stated amount of Span® 80 was sprayed on as a 25% by weight solution in diethylene glycol monobutyl ether and mixed in for 10 minutes.

The mixer speed was 125 rpm.

In those examples in which the aqueous aluminum sulfate was sprayed on, additional drying was carried out. Drying was done at 70° C., at a pressure of 150 mbar in the course of the residence time of 16 hours. The drying was augmented by a gas stream of 200 l/h of nitrogen.

The results are summarized in the tables which follow.

TABLE 1

Examples based on Hysorb ® F

| Example | Additive 1 | Additive 2 | Additive 3 | Additive 4 | BA [g/g] | ST [sec] | SV [%] |
|---|---|---|---|---|---|---|---|
| 1 | | | | | 16.5 | >600 | 0 |
| 2 | 0.06% Aerosil R 8200 | | 4%$Al_2(SO_4)_3$ | | | 77 | 65 |
| 3 | 0.17% Aerosil R 8200 | | 4%$Al_2(SO_4)_3$ | | 7.5 | 93 | 60 |
| 4 | 0.25% Aerosil R 812 | 1% Aerosil 200 | | | 19.8 | 300 | 20 |
| 5 | 0.5% Aerosil R 974 | 2% Aerosil 200 | | | 16.1 | 265 | 25 |
| 6 | | | 1%$Al_2(SO_4)_3$ | | 18.9 | >1500 | 0 |
| 7 | | | 5%$Al_2(SO_4)_3$ | | 21.0 | 270 | 0 |
| 8 | | | 10%$Al_2(SO_4)_3$ | | 22.5 | 174 | 0 |
| 9 | 0.5% Aerosil R 974 | | | | 12.3 | >600 | 100 |
| 10 | 2% Aerosil R 974 | | | | 5.6 | >600 | 100 |
| 11 | | | | 0.1% Span 80 | 13.4 | >600 | 0 |
| 12 | | | | 0.25% Span 80 | 17.7 | >600 | 0 |
| 13 | | | | 0.5% Span 80 | 18.4 | 2100 | 0 |
| 14 | | | | 1% Span 80 | 16.3 | >1200 | 0 |
| 15 | | 0.1% Aerosil 200 | 4%$Al_2(SO_4)_3$ | | 18.9 | 120 | 0 |
| 16 | | 0.3% Aerosil 200 | 4%$Al_2(SO_4)_3$ | | 19.5 | 138 | 0 |
| 17 | | 0.5% Aerosil 200 | 4%$Al_2(SO_4)_3$ | | 19.7 | 120 | 0 |
| 18 | | 1% Aerosil 200 | 4%$Al_2(SO_4)_3$ | | 20.2 | >600 | 0 |
| 19 | | 0.5% Aerosil 200 | 4%$Al_2(SO_4)_3$ | 0.5% Span 80 | 15 | 150 | 20 |
| 20 | | | 1%$Al_2(SO_4)_3$ | 0.25% Span 80 | 17.6 | 264 | 0 |
| 21 | | | 4%$Al_2(SO_4)_3$ | 1% Span 80 | 20.9 | 189 | 0 |
| 22 | | 0.5% Aerosil 200 | | 0.25% Span 80 | 18.4 | >600 | 100 |
| 23 | | 1% Aerosil 200 | | 0.1% Span 80 | 16.7 | >600 | 100 |
| 24 | 0.5% Aerosil R 974 | | 1%$Al_2(SO_4)_3$ | | 20.2 | 280 | 100 |
| 25 | 1% Aerosil R 974 | | 4%$Al_2(SO_4)_3$ | | 17.4 | 414 | 100 |
| 26 | 0.5% Aerosil R 974 | 0.5% Aerosil 200 | 4%$Al_2(SO_4)_3$ | 0.25% Span 80 | 19.7 | 66 | 70 |
| 27 | 0.75% Aerosil R 974 | 1% Aerosil 200 | 4%$Al_2(SO_4)_3$ | 0.25% Span 80 | 28.2 | 60 | 70 |
| 28 | 0.25% Aerosil R 974 | 0.5% Aerosil 200 | 4%$Al_2(SO_4)_3$ | 0.25% Span 80 | 22.8 | 60 | 80 |
| 29 | 0.5% Aerosil R 974 | 0.5% Aerosil 200 | 4%$Al_2(SO_4)_3$ | 0.25% Span 80 | 27.7 | 48 | 80 |
| 30 | | 1% Aerosil 200 | | | 16.9 | >600 | 0 |

TABLE 1-continued

| Examples based on Hysorb ® F | | | | | | | |
|---|---|---|---|---|---|---|---|
| Example | Additive 1 | Additive 2 | Additive 3 | Additive 4 | BA [g/g] | ST [sec] | SV [%] |
| 31 | | 2% Aerosil 200 | | | 17.7 | >600 | 0 |

Hysorb ® F: superabsorbent hydrogel (BASF Aktiengesellschaft, Germany)
Aerosil ® R 812: hydrophobicized pyrogenic silica (Degussa, Germany)
Aerosil ® R 974: hydrophobicized pyrogenic silica (Degussa, Germany)
Aerosil ® R 8200: hydrophobicized pyrogenic silica (Degussa, Germany)
Aerosil ® 200: hydrophilic pyrogenic silica (Degussa, Germany)
Span ® 80: sorbitan monooleate (Uniqema, Netherlands)

The spraying with aluminum sulfate solution (Examples 6 to 8) leads to a slightly improved blood absorbence and to a somewhat shorter solidification time. The amounts of aluminum sulfate required for this are high. The floatability of the hydrogels treated with aluminum sulfate only is inadequate.

The blending with hydrophobicized pyrogenic silica (Examples 9 and 10) leads to floatable hydrogels, but blood absorbence is dramatically decreased.

The spraying with Span® 80 (Examples 11 to 14) does not lead to improved product properties. This also applies to blending with pyrogenic silica (Examples 30 and 31).

Hence, none of the aftertreatments by themselves leads to products having the properties of the present invention.

Aftertreating the dried hydrogel with small amounts of hydrophobicized silica gives hydrogels possessing excellent floatability. In Example 3, 0.35% by weight of polyethylene glycol having an average molecular weight of 300 g/mol was additionally added to improve the bonding of the silica gel particles to the hydrogel.

The blending with pyrogenic silica and hydrophobicized pyrogenic silica (Examples 4 and 5) leads to hydrogels having excellent floatability.

The use of pyrogenic silica together with aluminum sulfate solution (Examples 15 to 18) leads to enhanced blood absorbence and to a shorter solidification time. But the aftertreated hydrogels are not floatable.

The use of Span® 80 together with aluminum sulfate solution (Examples 20 and 21) likewise leads to enhanced blood absorbence and a shorter solidification time. But the aftertreated hydrogels again are not floatable.

The use of Span® 80 together with pyrogenic silica (Examples 22 and 23) leads to floatable hydrogels. The disadvantage is that there are no sinking hydrogel fractions and that the solidification time has not been shortened.

Similarly, the use of aluminum sulfate solution and of hydrophobicized pyrogenic silica (Examples 24 and 25) leads to floatable hydrogels. But here again there is a disadvantage in that there are no sinking hydrogel fractions. Blood absorbence is slightly enhanced and solidification time is slightly shorter.

The three-stage aftertreatment of a) spraying with aluminum sulfate solution, b) blending with pyrogenic silica and c) spraying with Span® 80 solution (Example 19) gives a hydrogel having good floatability and a shorter solidification time. But blood absorbence is down compared with the starting material.

A very particularly advantageous performance profile is achieved with the four-stage aftertreatment of a) spraying with aluminum sulfate solution, blending with b) pyrogenic silica and c) hydrophobicized pyrogenic silica and also d) spraying with Span® 80 solution (Examples 26 to 29). The hydrogels thus aftertreated exhibit a distinctly improved blood absorbence and also optimum floatability. The hydrogel floats to some extent on the solution and the swelling hydrogel hence blocks off the surface of the liquid in the upward direction, on the other hand there are sinking hydrogel fractions and, owing to the improved blood absorbence, they lead to a very short solidification time.

We claim:

1. A hydrogel having a floatability and having a thickening capability wherein the hydrogel thickens from 40% to 90% of an aqueous solution or suspension starting from the surface of the solution or suspension and the hydrogel thickens the rest of the solution or suspension starting from the bottom of a container for the solution or suspension, said hydrogel comprising superabsorbent polymer particles coated with 0.05% to 1%, by weight, of a hydrophobic compound, wherein the hydrophobic compound is a hydrophobicized silica or a hydrophobicized mixture of silicas and aluminas, and 0.05% to 4%, by weight, of a multivalent cation; and said hydrogel having a solidification time of less than 120 seconds upon contact with the solution or suspension and having a blood absorbance of at least 10 g/g.

2. A hygiene article comprising a hydrogel of claim 1, said hygiene article selected from the group consisting of an incontinence article, a napkin, a tampon, and a liner.

3. A method of absorbing blood, body fluids, or both comprising contacting the blood, body fluid, or both with a hydrogel of claim 1.

4. The method of claim 3 wherein the hydrogel is present in a hygiene article.

5. A method of thickening an aqueous solution or suspension comprising contacting the solution or suspension with a hydrogel of claim 1.

6. A method of thickening medical wastes comprising contacting the medical waste with a hydrogel of claim 1.

7. A composition comprising a hydrogel of claim 1 and one or more of a biocidal material, an antimicrobial material, an antibacterial material, a perfume or scent material, a stabilizer, a dye, and a pH indicator.

8. The hydrogel of claim 1 wherein the hydrophobic compound is particles having an average diameter from 0.001 to 10 μm.

9. The hydrogel of claim 1 wherein the hydrogel further comprises a surfactant.

10. The hydrogel of claim 9 wherein the surfactant is a sorbitan ester.

11. The hydrogel of claim 1 wherein the multivalent cation is an aluminum ion.

12. The hydrogel of claim 1 further comprising a hydrophilic compound.

13. The hydrogel of claim 12 wherein the hydrophilic compound is a silica or a mixture of silicas and aluminas.

* * * * *